United States Patent [19]

Schneider et al.

[11] Patent Number: 5,028,728

[45] Date of Patent: Jul. 2, 1991

[54] PROCESS FOR THE PREPARATION OF REACTION PRODUCTS OF 2,2-BIS-(4-HYDROXPHENYL)-HEXAFLUOROPROPANE AND NEW DERIVATIVES OF THIS TYPE

[75] Inventors: Klaus-Albert Schneider, Hattersheim am Main; Günter Siegemund, Hofheim am Taunus, both of Fed. Rep. of Germany

[73] Assignee: Hoechst Aktiengesellschaft, Frankfurt, Fed. Rep. of Germany

[21] Appl. No.: 515,202

[22] Filed: Apr. 27, 1990

Related U.S. Application Data

[62] Division of Ser. No. 152,432, Feb. 5, 1988, abandoned.

[30] Foreign Application Priority Data

Feb. 10, 1987 [DE] Fed. Rep. of Germany ....... 3704005

[51] Int. Cl.$^5$ ................ C07C 303/00; C07C 307/00; C07C 309/00; C07C 311/00
[52] U.S. Cl. ....................................... 558/47; 558/46; 564/330
[58] Field of Search ................................. 558/47, 46

[56] References Cited

U.S. PATENT DOCUMENTS 2,034,491 5/1933 Sloan .................................... 564/330
3,346,612 10/1967 Hansen ................................ 558/47

FOREIGN PATENT DOCUMENTS 61-189231 8/1986 Japan .

OTHER PUBLICATIONS

Lau, K. S. Y., et al., *J. Polymer Sci.*, 20(9), pp. 2381-2393, (1982).
Lau, K. S. Y., et al., *J. Polymer Sci., 21,* pp. 3009-3026, (1983).

*Primary Examiner*—Glennon H. Hollrah
*Assistant Examiner*—Scott C. Rand
*Attorney, Agent, or Firm*—Connolly & Hutz

[57] ABSTRACT

Process for the preparation of compounds of the formula I

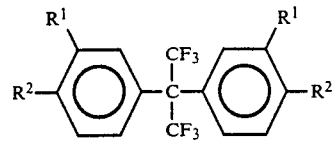

in which
 $R^1$ denotes $NO_2$ or $NH_2$ and
 $R^2$ denotes a radical of a cycloaliphatic amine having 6 ring atoms and a total of not more than 10 carbon atoms, a benzylamine radical, an aniline radical which contains up to three substituents belonging to the group comprising alkyl, alkoxy, chlorine and bromine, not more than two of which can be halogen and not more than one of which can be alkoxy, and contains a total of not more than 10 carbon atoms, or which contains a trifluoromethyl or phenoxy group, or $R^2$ denotes the phenylmercapto radical or the benzylmercapto radical, compounds of the formula I in which $R^1$ is $NO_2$ or $NH_2$ and $R^2$ denotes a radical of a cycloaliphatic amine having 6 ring atoms and a total of not more than 10 carbon atoms, a benzylamine radical, an aniline radical which contains at least one, but up to three, substituents belonging to the group comprising alkyl, alkoxy, chlorine and bromine, not more than two of which can be halogen and not more than one of which can be alkoxy, and contains a total of not more than 10 carbon atoms, or which contains a trifluoromethyl group, or $R^2$ denotes the phenylmercapto radical or the benzylmercapto radical, and also compounds of the formula II

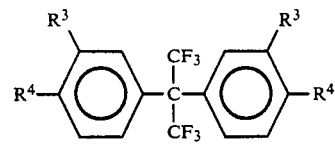

in which $R^3$ denotes hydrogen or $NO_2$ and $R^4$ denotes OMes, OTos or OBros, and also a process for the preparation of compounds of the formula II.

3 Claims, No Drawings

PROCESS FOR THE PREPARATION OF REACTION PRODUCTS OF 2,2-BIS-(4-HYDROXPHENYL)-HEXAFLUORO-PROPANE AND NEW DERIVATIVES OF THIS TYPE

This is a division of U.S. application Ser. No. 152,432 filed Feb. 5, 1988, now abandoned, by Klaus-Albert Schneider and Gunter Siegemund.

It is known that 2,2-bis-[3-amino-4-(4-phenoxyanilino)-phenyl]-hexafluoropropane and 2,2-bis-(3-amino-4-anilino-phenyl) -hexafluoropropane can be prepared from 2,2-bis -(4-hydroxyphenyl)-hexafluoropropane (K.S.Y. LAU, A. L. LANDIS, W.J. KELLEGHAN and C.D. BEARD, J. Polym. Sci., Polym. Chem. Ed. 20, 1982, (9), 2381-93 and K.S.Y. LAU, W.J. KELLEGHAN, R.H. BOSCHAN and N. BILOW, J. Polym. Sci., Polym. Chem. Ed. 1983, 21 (10), 3009-11, 14 and 21). In this reaction, both of the phenolic groups of the starting material 2,2-bis-(4-hydroxyphenyl)-hexafluoropropane are converted into $CF_3-SO_2-O-$(triflate) groups using trifluoromethanesulfonic anhydride, which is difficult to handle and expensive. In the subsequent process step, the ditriflate prepared in this manner is converted into 2,2-bis-(3-nitro-4-triflatophenyl)-hexafluoropropane by means of nitrating acid at 100° C. This produces in the aromatic ring a position which is strongly activated toward nucleophilic attack, since triflate groups are, as is known, groups which can be split off very readily. In the third process step, the two triflate groups are then replaced in a nucleophilic substitution reaction by either two 4-phenoxyanilino groups or two anilino groups. In the last step of the process, the corresponding aromatic tetramines are set free by catalytic reduction of the two nitro groups.

The disadvantages of the abovementioned process, particularly in regard to preparation on an industrial scale, are the reaction with trifluoromethanesulfonic anhydride, which is difficult to control, and the nitration with nitrating acid at 100° C. The cost of trifluoromethanesulfonic anhydride, but particularly the handling of this dangerous chemical and also the handling of hot nitrating acid, which entails safety risks, makes an improvement of the process desirable.

It has now been found, surprisingly, that the known compounds 2,2-bis-(3-amino-4-anilinophenyl)-hexafluoropropane and 2,2-bis-[3-amino-4-(4-phenoxyanilino)-phenyl]-hexafluoropropane and other aromatic tetramines can be prepared by a process which eliminates the disadvantages mentioned above. The key compounds in this new process are novel intermediates of the formula II (see patent claim 9) in which $R^3$ represents hydrogen or $NO_2$ and $R^4$ represents OMes (1), OTos (2)- or OBros (3). In these abbreviations, Mes denotes the methanesulfonyl radical, Tos the toluenesulfonyl radical and Bros the bromophenylsulfonyl radical.

The readily preparable compounds of the formula II in which $R^3$ denotes $NO_2$ can be reacted with nucleophiles which still have at least one free hydrogen atom. Suitable nucleophiles are, above all, primary and secondary amines, such as aniline, phenoxyaniline, aniline derivatives which additionally contain, on the ring, up to three substituents having a total of 1 to 4 carbon atoms, such as alkyl groups and/or an alkoxy group, or contain other electron-releasing substituents, such as bromine and/or chlorine, or, instead of these, also electron-attracting substituents, such as the trifluoromethyl group; and also mercaptans. Among the amines, primary amines are preferred, so that compounds of the formula I (see patent claim 1) in which $R^2$ is an amine radical in which a hydrogen atom is still attached to the nitrogen atom of the radical are formed. Specific examples which may be mentioned are the various toluidines, xylidines, ethylanilines, propylanilines, butylanilines or the amino derivative of cymene, and also the various methoxyanilines, ethoxyanilines, propoxyanilines and butoxyanilines, including in each case the isomeric forms of the propyl and butyl radicals, thus, for example, the amino derivative of cymene and also the bromine and chlorine derivatives thereof in which these halogens are present on the ring. Preferred compounds are those which are unsubstituted or contain only one substituent and, among the substituted compounds, in particular those containing the substituent in the p-position, such as 4-methoxyaniline. Suitable amines are also cyclohexylamine, the hydrogenation product of benzylamine and alkyl derivatives of these amines having up to 10 carbon atoms, the alkyl radicals thus representing one or more of the radicals methyl, ethyl, n-propyl and isopropyl and the various butyl radicals. Further suitable compounds are the trifluoromethylanilines, particularly 4-trifluoromethylaniline, benzylamine, thiophenol and benzyl mercaptan. In all cases nucleophilic attack takes place at the aromatic ring with the elimination of the mesylate, tosylate or brosylate groups.

The invention therefore relates to a process for the preparation of compounds of the formula I (see patent claim 1) in which $R^1$ denotes $NO_2$ or $NH_2$ and $R^2$ denotes a radical of a cycloaliphatic amine having 6 ring atoms and a total of not more than 10 carbon atoms, which thus contains one or more of the radicals methyl, ethyl, n-propyl, isopropyl and the various butyl radicals, a benzylamine radical, an aniline radical which is unsubstituted or contains up to three substituents from the group consisting of alkyl, alkoxy, chlorine and bromine, not more than two of which can be halogen and not more than one of which can be alkoxy, and contains a total of not more than 10 carbon atoms, or which contains a trifluoromethyl or phenoxy group, or $R^2$ denotes the phenylmercapto or benzylmercapto radical, which comprises a₁) reacting 2,2-bis-(4-hydroxyphenyl)-hexafluoropropane with a mesyl, tosyl or brosyl halide to give the intermediates 2,2-bis-(4-mesyloxyphenyl)-hexafluoropropane, 2,2-bis-(4-tosyloxyphenyl)-hexafluoropropane or 2,2-bis(4-brosyloxyphenyl)-hexafluoropropane, respectively, (i.e. compounds of the formula II in which $R^3=H$), and then nitrating these intermediates with nitric acid to give the intermediates 2,2-bis-(4-mesyloxy-3-nitrophenyl)-hexafluoropropane, 2,2-bis-(3-nitro-4-tosyloxyphenyl)-hexafluoropropane or 2,2-bis-(4-brosyloxy-3-nitrophenyl)hexafluoropropane, respectively, (i.e. compounds of the formula II in which $R^3=NO_2$) or a₂) reacting 2,2-bis-(4-hydroxy-3-nitrophenyl)-hexafluoropropane with a mesyl, tosyl or brosyl halide to give the intermediates mentioned in a1), 2,2-bis-(4-mesyloxy-3-nitrophenyl) -hexafluoropropane, 2,2-bis-(3-nitro-4-tosyloxyphenyl) -hexafluoropropane or 2,2-bis-(4-brosyloxy-3-nitrophenyl)-hexafluoropropane, respectively, (i.e. compounds of the formula II in which $R^3=NO_2$) and b) then reacting these compounds with the amine corresponding to the meaning of $R^2$ or with thiophenol or benzylmercaptan to give compounds of the formula I in which $R^1$ denotes $NO_2$, the halogen of the mesyl, tosyl and brosyl halide having an atomic weight between 35 and 80, thus being chlorine or bromine, and c) isolating the compounds obtained in accordance with b) or hydrogenating them catalytically to give compounds of the formula I in which $R^2$ denotes $NH_2$.

The invention also relates to compounds of the formula I in which $R^1$ is $NO_2$ or $NH_2$ and $R^2$ has the meaning indicated above, but is other than the anilino and phenoxyanilino radical.

The invention also relates to compounds of the formula II in which $R^3$ denotes hydrogen or $NO_2$ and $R^4$ denotes OMes, OTos or OBros and to a process for their preparation which comprises α) reacting 2,2-bis-(4-hydroxyphenyl)-hexafluoropropane or 2,2-bis-(4-hydroxy-3-nitrophenyl)-hexafluoropropane with mesyl, tosyl or brosyl chloride or mesyl, tosyl or brosyl bromide, or β) nitrating 2,2-bis-(4-mesyloxyphenyl)- or 2,2-bis-(4-tosyloxyphenyl) - or 2,2-bis-(4-brosyloxyphenyl)-hexafluoropropane with nitric acid. By the process according to the invention, the new 2,2-bis -(4-methyloxy- or 2,2-bis-(4-tosyloxy- or 2,2-bis (4-brosyloxy-3-nitrophenyl)-hexafluoropropanes or their analogues which are each unsubstituted in the 3-position are obtained by various routes from 2,2-bis-(4-hydroxyphenyl)-hexafluoropropane (bisphenol AF), which is readily accessible, in the form of new, reactive intermediates suitable for aromatic substitution reaction. These intermediates are particularly advantageous starting materials for the synthesis of aromatic diamines and tetramines.

It is a particular advantage of the invention that the nitro compounds of the formula II (9, 10 and 11) can be prepared in only two process steps, starting from bisphenol AF, namely by nitration with nitric acid and reaction with a mesyl, tosyl or brosyl halide, preferably a mesyl, tosyl or brosyl chloride, in any desired sequence. In principle, both routes are of equal value (see scheme 1). In the first possible route, 2,2-bis-(4-hydroxyphenyl)-hexafluoropropane is nitrated under conditions such as are customary for the introduction of a single nitro group into a phenolic nucleus - preferably using half-concentrated nitric acid - to give 2,2-bis-(4-hydroxy -3-nitrophenyl)-hexafluoropropane -,8 which is converted to the intermediates 9, 10 and 11 in a second process step in a conventional manner by means of the corresponding acid halide in the presence of a base, for example a tertiary amine, such as triethylamine, tripropylamine, triisopropylamine and one of the various tributylamines, or preferably pyridine. As an alternative, it is also possible to react 2,2-bis-(4-hydroxyphenyl)hexafluoropropane 4 under customary conditions with the corresponding acid halide in the presence of a base, and then to react the products under conditions such as are customary for the introduction of a single nitro group into the aromatic nucleus of esters of phenols - preferably using half-concentrated nitric acid - to give the same products 9, 10 and 11. The yields of the individual reaction steps are all between 80 and 95%.

The 3-nitro compounds of the formula II can be reacted, according to the invention, in nucleophilic aromatic substitution reactions with a large number of primary and secondary amines or with thiophenol or benzylmercaptan, which are inexpensive and easy to handle, by replacing the mesyloxy, tosyloxy or brosyloxy groups, to give a series of interesting, predominantly new, aromatic compounds, shown in scheme 2. Some representative reactions employing 9 are shown in this scheme. If the 3-nitro compounds of the formula II are reacted with aniline or 4-phenoxyaniline, 2,2-bis-(3-amino-4-anilinophenyl) -hexafluoropropane or 2,2-bis-[3-amino-4-(4-phenoxyanilino) -phenyl]-hexafluoropropane which is already known and has been prepared by another route is obtained after catalytic hydrogenation. In addition to these two known tetramines, the process according to the invention leads, in accordance with claim 1, to a number of new aromatic tetramines and diaminodimercapto compounds.

The process is carried out particularly advantageously with mesyl chloride, because the latter is liquid; the process is described in schemes 1, 2 and 3.

In order to obtain the appropriate tetramino or diaminodimercapto compound, the dinitro compounds mentioned in scheme 2 are reduced catalytically with hydrogen under customary hydrogenation conditions (cf. scheme 3), for example using platinum, palladium or nickel catalysts on customary supports, such as carbon. The intermediates and end products prepared in this manner, such as 2,2-bis-(4-mesyloxyphenyl)-hexafluoropropane, 2,2-bis-(4-mesyloxy-3-nitrophenyl)-hexafluoropropane, the corresponding tosyl and brosyl analogues of the formula II (see patent claim 9) and the compounds of the general formula I (see patent claim 2) are new. Fluorinated aromatic diamines and tetramines of this type are valuable monomers for polybenzimidethiazoles and polybenzimidazoles. The introduction of the hexafluoroisopropylidene units results, in the case of such polymers, in an enormous improvement in various physical or physico-chemical properties, such as thermal stability and dielectric properties.

In what follows, the preparation of the starting material for variant $a_2$) is described first, and the method of carrying out the process according to the invention and the preparation of compounds according to the invention are described subsequently. The ethanol used is 96% pure. M.p. denotes melting point.

Starting material for variant $a_2$) 2,2-Bis-(4-hydroxy-3-nitrophenyl)-hexafluoropropane 924 g of dilute nitric acid prepared from 439 ml of 98% strength nitric acid and 561 ml of water are added dropwise, at a reaction temperature of 15–25° C. and with vigorous stirring, to a mixture of 302.4 g (0.9 mol) of bisphenol AF and 1,000 ml of chloroform. Stirring is continued at this temperature for one hour in order to complete the reaction. The organic phase is then separated off and the aqueous phase is extracted three times with dichloromethane. The combined organic phases are washed until neutral with sodium bicarbonate solution and are dried over $MgSO_4$. After the solvent has been removed, 427 g of a viscous oil are obtained as crude product from which 322 g (84% yield) of 2,2-bis-(4-hydroxy-3-nitrophenyl) -hexafluoropropane are isolated after recrystallization from ethanol. M.p. 116–119° C.

IR (KBr): $\nu = 1540, 1340$ cm$^{-1}$ ($NO_2$), 1280–1140 cm$^{-1}$ ($CF_3$).

$^1$H (CDCl$_3$): $\delta = 10.7$ (s, broad; 2H, hydroxyl), 8.3 (d, $^4J$H,H=2 Hz, 2H, aromatic), 7.6 (d, d, $^3J$H,H=9 Hz, $^4J$H,H=2 Hz, 2H, aromatic) 7.3 (d, $^3J$H,H=9 Hz, 2H, aromatic) $^{13}$C (CDCl$_3$): $\delta = 155.5, 138.1, 133.3, 126.9, 124.3, 120.8,$ (aromatic), 123.4 (9, $^1J$C,F=287 Hz, CF$_3$), 63.3 (sept., $^2J$C,F=28 Hz, C(CF$_3$)$_2$).

$^{19}$F (CDCl$_3$): $\delta = -64.7$ (CF$_3$).

$C_{15}H_8F_6N_2O_6$: Calculated % C 42.3 H 1.9 F 26.7 N 6.6 O 22.0.

EXAMPLES

2,2-Bis-(4-mesyloxy-3-nitrophenyl)-hexafluoropropane

A) 11.5 g (0.1 mol) of methanesulfonyl chloride are added dropwise, at a reaction temperature of 0–5° C., to a mixture of 21.3 g (0.05 mol) of 2,2-bis-(4-hydroxy-3-nitrophenyl)-hexafluoropropane and 100 ml of pyridine. Stirring is continued for 1 hour at 5° C. and overnight at room temperature. The reaction mixture is then acidified, first with dilute hydrochloric and then with half-concentrated hydrochloric acid; the precipitate which is deposited is filtered off with suction and washed with water until neutral. The crude product (29.3 g) is then recrystallized from toluene, resulting in 24.8 g of analytically pure 2,2-bis-(4-mesyloxy-3-nitrophenyl)-hexafluoropropane to be isolated. Yield 85%; m.p. 119–121° C.

IR (KBr): $\nu$=1540, 1340 cm$^{-1}$ (NO$_2$), 1360, 1090 cm$^{-1}$ (—SO$_2$O—), 1280–1140 cm$^{-1}$ (CF$_3$).

$^1$H (CDCl$_3$): $\delta$=8.1 (mc, 2H, aromatic), 7.6 (mc, 4H, aromatic), 3.4 (s, 6H, CH$_3$).

C$_{17}$H$_{12}$F$_6$N$_2$O$_{10}$S$_2$: Calculated % C 35.1 H 2.1 F 19.6 (582.4) N 4.8 S 11.0 Found % C 35.3 H 2.1 F 19.4 N 5.1 S 11.3.

B) In an alternative procedure, 68.9 g (0.14 mol) of 2,2-bis-(4-mesyloxyphenyl)-hexafluoropropane are introduced, in portions and at a reaction temperature of 0–10° C., into 90 ml of 98% strength nitric acid.

Stirring is then continued overnight at room temperature. After the product has been hydrolysed with ice water, the organic phase is separated off and the aqueous phase is extracted four times with dichloromethane. The combined organic phases are washed until neutral with dilute sodium bicarbonate solution and are dried over MgSO4. Removing the solvent and recrystallizing the product gives 75 g (92% yield) of 2,2-bis-(4-mesyloxy-3-nitrophenyl)-hexafluoropropane.

2) 2,2-Bis-(4-mesyloxyphenyl)-hexafluoropropane 11.8 g (0.1 mol) of methanesulfonyl chloride are added dropwise, at a reaction temperature of 0–5° C., to a solution of 16.8 g (0.05 mol) of bisphenol AF in 100 ml of pyridine. Stirring is then continued for a further hour at 5° C. and overnight at room temperature. The reaction mixture is then acidified with sufficient half-concentrated hydrochloric acid to precipitate the product. Filtering off with suction and washing with water gives 24 g of crude product, and recrystallization from toluene gives 20.2 g (82% yield) of 2,2-bis-(4-mesyloxyphenyl)-hexafluoropropane are isolated. M.p 136–138° C.

IR (KBr): $\nu$=1370 cm$^{-1}$ (—SO$_2$O—), 1290–1150 cm$^{-1}$ (CF$_3$).

$^1$H (CDCl$_3$): $\delta$=7.4 (mc, 8H, aromatic), 3.2 (s, 6H, CH$_3$).

C$_{17}$H$_{14}$F$_6$O$_6$S$_2$: Calculated % C 41.5 H 2.9 F 23.1 (492.4) S 13.0 Found % C 41.4 H 2.7 F 23.0 S 13.4

3) 2,2-Bis-(3-nitro-4-tosyloxyphenyl)-hexafluoropropane 11.5 g (0.205 mol) of potassium hydroxide are added to a solution of 42.6 g (0.1 mol) of 2,2-bis-(4-hydroxy-3-nitrophenyl)-hexafluoropropane and 39.1 g (0.205 mol) of p-toluenesulfonyl chloride in 300 ml of methylene chloride. The reaction mixture is then stirred at room temperature for five hours, in the course of which it turns an orange-yellow color. After precipitated potassium chloride (16 g) has been removed, the filtrate is dried over MgSO4. Removing the solvent and recrystallizing from toluene gives 43 g of 2,2-bis-(3-nitro-4-tosyloxyphenyl)-hexafluoropropane. Yield 58%; m.p. 206–208° C.

$^1$H (DMSO): $\delta$=8–7.3 (m, 14H, aromatic), 2.4 (s, 6H, 2 CH$_3$)

$^{19}$F (DMSO): $\delta$=−63.1 (s, 2 CF$_3$).

C$_{29}$H$_{20}$F$_6$N$_2$O$_{10}$S$_2$: Calculated % C 47.4 H 2.7 N 3.8 S 8.7 F 15.5 (734.6) Found % C 48.0 H 2.9 N 3.8 S 8.2 F 15.8

4) Preparation of 2,2-bis-(4-anilino-3-nitrophenyl)-hexafluoropropane

A) A solution of 60 g (0.103 mol) of 2,2-bis-(4-mesyloxy-3-nitrophenyl)-hexafluoropropane and 122.8 g (1.32 mol) of aniline in 400 ml of acetonitrile is heated under reflux for 24 hours. In the course of this the methanesulfonic acid salt of aniline is precipitated, and is removed by filtration with suction. The filtrate is freed from the solvent and from excess aniline by distillation under reduced pressure. Recrystallizing the residue from ethanol gives 47.3 g of 2,2-bis-(4-anilino-3-nitrophenyl)-hexafluoropropane (80% yield). M.p. 165–166° C.

IR (KBr): $\nu$=3370 cm$^{-1}$ (broad, NH), 1520, 1320 cm$^{-1}$ (NO$_2$), 1280–1150 cm$^{-1}$ (CF$_3$).

$^1$H (CDCl$_3$): $\delta$=9.6 (s, broad, 2H, NH), 8.3 (mc, 2H, aromatic), 7.3 (mc, 14H, aromatic).

C$_{27}$H$_{18}$F$_6$N$_4$O$_4$ Calculated % C 56.2 H 3.1 F 19.8 N 9.7 O 11.1 (576.5) Found % C 56.0 H 3.1 F 19.7 N 9.4 O 11.4.

B) In an alternative procedure, 7.3 g (0.01 mol) of 2,2-bis-(3-nitro-4-tosyloxyphenyl)-hexafluoropropane, 11.6 g (0.125 mol) of aniline and 50 ml of acetonitrile are heated under reflux for 24 hours. After the red-orange suspension has been cooled, the solid is removed and washed with acetonitrile. The solvent is removed from the filtrate, and the product is recrystallized twice from ethanol to give 6.3 g of 2,2-bis-(4-anilino-3-nitrophenyl)-hexafluoropropane (65% yield).

5) Preparation of 2,2-bis-(3-amino-4-anilinophenyl)-hexafluoropropane 34.6 g (0.06 mol) of 2,2-bis-(4-anilino-3-nitrophenyl)-hexafluoropropane in 220 ml of ethanol are reduced with hydrogen under the catalytic action of 2 g of Pd-on-C (5% by weight in active charcoal) in a 500 ml chromium nickel steel autoclave. The crude product (30.7 g - pure according to H-NMR) is filtered off and recrystallized twice to give 15.1 g of analytically pure 2,2-bis-(3-amino-4-anilinophenyl) -hexafluoropropane (49% yield). The melting point is 177–178° C., and differs from the melting point given in the literature (120° C.).

IR (KBr): $\nu$=3550–2350 cm$^{-1}$ (broad, NH, NH$_2$), 1280–1120 cm$^{-1}$ (CF$_3$).

$^1$H (CDCl$_3$): $\delta$=7.0 (mc, 16H, aromatic), 5.3 (s, broad, 2H, NH), 3.7 (s, broad, 4H, NH$_2$).

C$_{27}$H$_{22}$F$_6$N$_4$: Calculated % C 62.8 H 4.3 F 22.1 N 10.8 (516.5) Found % C 63.0 H 4.3 F 22.4 N 10.8

6) 2,2-Bis-(4-benzylamino-3-nitrophenyl)-hexafluoropropane

A solution of 107.1 g (1 mol) of benzylamine in 100 ml of acetonitrile is added dropwise, at a reaction temperature of 20–30° C., to a solution of 58.4 g (0.1 mol) of 2,2-bis -(4-mesyloxy-3-nitrophenyl)-hexafluoropropane in 700 ml of acetonitrile. When the slightly exothermic reaction has subsided, the mixture is boiled under reflux for a further 4 hours to complete the reaction. The product precipitates when the reaction mixture is cooled. After being filtered off with suction and recrystallized from ethanol, 40.7 g (67% yield) of 2,2-bis-(4-benzylamino-3-nitrophenyl)-hexafluoropropane are obtained. M.p. 168-172° C. This melting point was determined in a sealed melting point tube in order to prevent sublimation.

IR (KBr); $\nu = 3610-2250$ cm$^{-1}$ (NH), 1535, 1350 cm$^{-1}$ (NO$_2$), 1290-1110 cm$^{-1}$ (CF$_3$).

$^1$H (DMSO): $\delta = 7.8$ (d, $^{4J}$H,H=2 Hz, 2H aromatic), 7.4 (mc, 10H, aromatic), 7.0 (dd, $^{3J}$H,H=10 Hz, $^{4J}$H,H=2 Hz, 2H, aromatic), 6.6 (d, $^{3J}$H,H=10 Hz, 2H, aromatic), 4.0 (s, 4H, CH$_2$).

$^{19}$F (DMSO): $\delta = -63.4$ (CF$_3$).

C$_{29}$H$_{22}$F$_6$N$_4$O$_4$: high-resolution mol ion peak: Calculated 604.1535 Found 604.1545.

7)
2,2-Bis-(4-cyclohexylamino-3-nitrophenyl)-hexafluoropropane

This compound was prepared analogously to Example 6. M.p 205-208° C., yield 90%.

IR (KBr); $\nu = 3450$ cm$^{-1}$ (broad, NH), 1530, 1360 cm$^{-1}$ (NO$_2$), 1300-1120 cm$^{-1}$ (CF$_3$).

$^1$H (DMSO): $\delta = 7.8$ (d. $^{4J}$H,H=2 Hz, 2H, aromatic), 7.4 (s, broad, 2H, NH), 6.9 (dd, $^{3J}$H,H=10 Hz, $^{4J}$H,H=2 Hz, 2H, aromatic), 6.5 (d, $^{3J}$H,H=10 Hz, 2H, aromatic), 1.5 (mc, 22H, aliphatic).

$^{19}$F (DMSO): $\delta = -63.4$ (CF$_3$).

8)
2,2-Bis-(4-phenylmercapto-3-nitrophenyl)-hexafluoropropane

A solution of 11.0 g (0.1 mol) of thiophenol in 40 ml of methylene chloride is added dropwise, at a reaction temperature of 20 to 30° C., to a solution of 29.1 g (0.05 mol) of 2,2-bis-(4-mesyloxy-3-nitrophenyl)-hexafluoropropane in 10.1 g (0.1 mol) of triethylamine and 60 ml of dichloromethane. Stirring is continued overnight. The reaction mixture is then hydrolysed and extracted three times with dichloromethane. The combined organic phases are washed with water and dried over MgSO4 and freed from the solvent by distillation. The residue is recrystallized from ethanol (74% yield).

M.p. 176-178° C.

IR (KBr); $\nu = 1520$, 1340 cm$^{-1}$ (NO$_2$), 1300-1110 cm$^{-1}$ (CF$_3$).

$^1$H (CDCl$_3$): $\delta = 8.2$ (d, $^{4J}$H,H=2 Hz, 2H, aromatic), 7.6 (mc, 10H, aromatic), 7.3 (d, broad, $^{3J}$H,H=8 Hz, aromatic), 6.8 (d, $^{3J}$H,H=8 Hz, 2H, aromatic).

$^{19}$F (CDCl$_3$): $\delta = -64.6$ (CF$_3$).

9)
2,2-Bis-(4-benzylmercapto-3-nitrophenyl)-hexafluoropropane

A solution of 29.7 g (0.051 mol) of 2,2-bis-(4-mesyloxy -3-nitrophenyl)-hexafluoropropane is added dropwise, at room temperature, to a suspension of 13.6 g (0.11 mol) of benzyl mercaptan and 15.2 g (0.11 mol) of K$_2$CO$_3$ in 100 ml of acetonitrile. The reaction is slightly exothermic.

Since the reaction mixture becomes more and more viscous during the course of the reaction, it must be diluted with a further 50 ml of acetonitrile. Stirring is continued overnight in order to complete the reaction. The reaction mixture is then hydrolysed and extracted, first with dichloromethane and then with diethyl ether. The combined organic phases are dried over MgSO4. Removing the solvent and recrystallizing the crude product from ethanol gives 21.5 g (66% yield) of 2,2-bis-(4-benzyl -mercapto-3-nitrophenyl)-hexafluoropropane.

M.p. 129-130° C.

IR (KBr): $\nu = 1520$, 1325 cm$^{-1}$ (NO$_2$), 1280-1150 cm$^{-1}$ (CF$_3$).

$^1$H (CDCl$_3$): $\delta = 8.3$ (s, broad, 2H, aromatic), 7.5 (mc, 14H, aromatic), 4.3 (s, 4H, CH$_3$).

C$_{29}$H$_{20}$F$_6$N$_2$O$_4$S$_2$: Calculated % C 54.5 H 3.1 F 17.8 N 4.4 S 10.0 (638.6) Found % C 54.5 H 2.9 F 17.5 N 4.4 S 10.4

10)
2,2-Bis-(3-amino-4-benzylmercaptophenyl)-hexafluoropropane

This compound was prepared analogously to the catalytic reduction with Pd-on-C described in Example 5.

IR (KBr); $\nu = 3600-2600$ cm$^{-1}$ (NH$_2$), 1300-1120 cm$^{-1}$ (CF$_3$).

$^1$H (CDCl$_3$): $\delta = 7.2$ (mc, 12H, aromatic), 6.6 (mc 4H, aromatic), 4.2 (s, broad, 4H, NH$_2$), 3.9 (s, 4H, CH$_2$).

$^{19}$F (CDCl$_3$): $\delta = -63.8$ (CF$_3$).

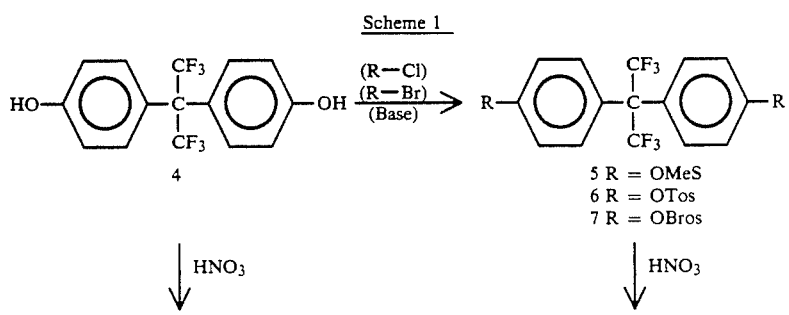

Scheme 1

4
5 R = OMeS
6 R = OTos
7 R = OBros

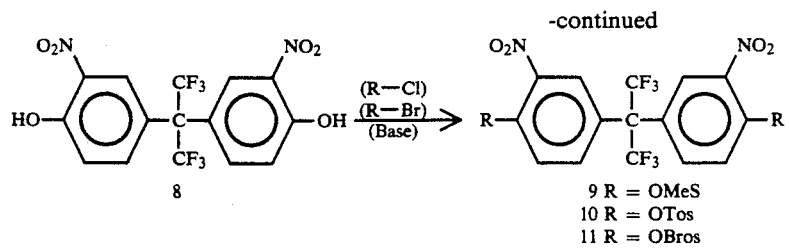
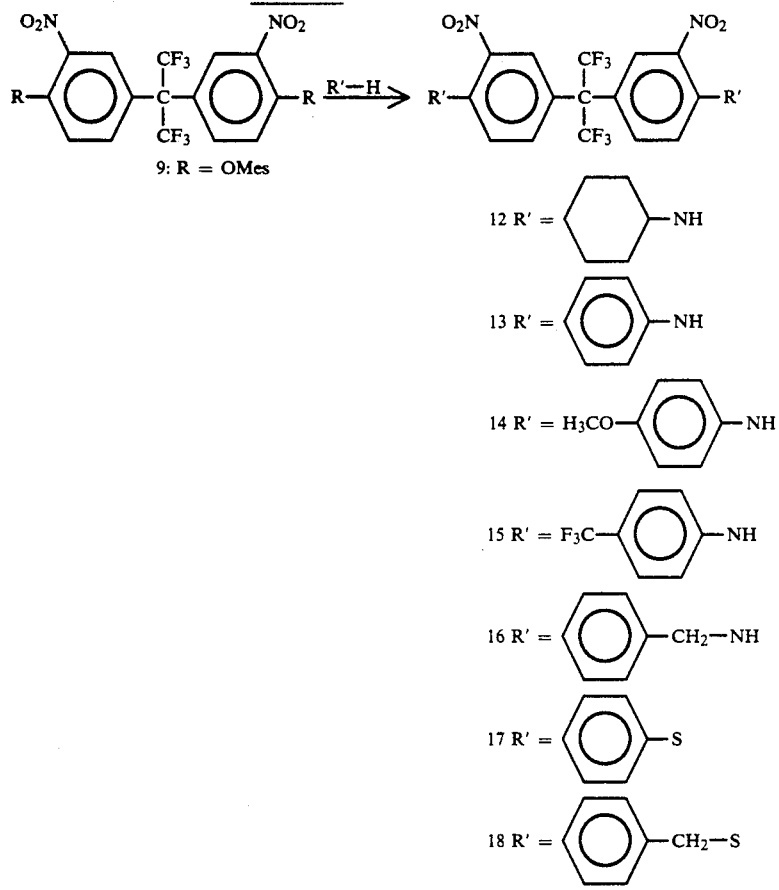
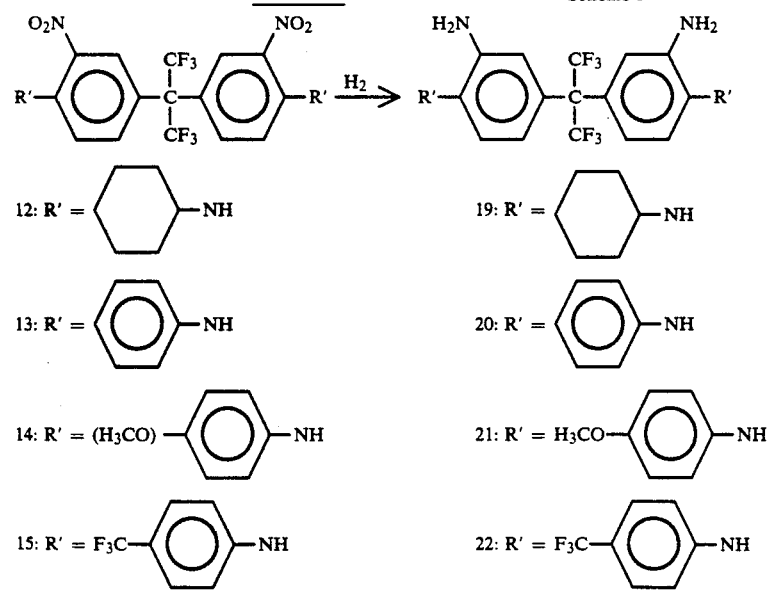

16: R' = 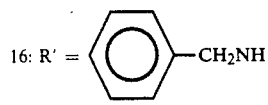
17: R' = 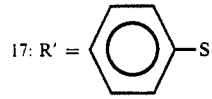
18: R' = 
23: R' = 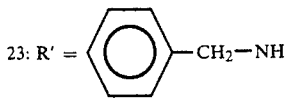
24: R' = 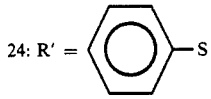
25: R' = 
We claim:
1. A compound of the formula II
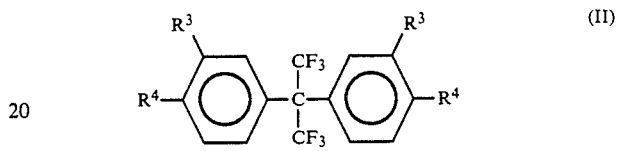
wherein $R^3$ represents hydrogen or $NO_2$ and $R^4$ represents O-mesyl, O-tosyl or O-brosyl.
2. A compound as claimed in claim 1, wherein $R^4$ represents O-mesyl.
3. A compound as claimed in claim 1 wherein $R^3$ represents $NO_2$ and $R^4$ represents O-mesyl.
* * * * *